United States Patent [19]
Gustafson

[11] Patent Number: 5,976,058
[45] Date of Patent: Nov. 2, 1999

[54] APPARATUS FOR EFFECTING STRETCHING OF INTRINSIC MUSCLES AND AN ASSOCIATED METHOD

[76] Inventor: Norman P. Gustafson, 2508 Collins Rd., Pittsburgh, Pa. 15235

[21] Appl. No.: 08/826,778

[22] Filed: Apr. 7, 1997

[51] Int. Cl.$^6$ .................................................. A61H 1/00
[52] U.S. Cl. ................... 482/44; 602/20; 601/40
[58] Field of Search ...................... 128/877, 878, 128/879; 602/20, 21; 601/40; 482/44, 48, 46

[56] References Cited

U.S. PATENT DOCUMENTS

| | | | |
|---|---|---|---|
| 3,769,970 | 11/1973 | Swanson | 602/21 |
| 4,441,490 | 4/1984 | Nirschl | 128/77 |
| 4,584,993 | 4/1986 | Nelson | 128/77 |
| 4,899,763 | 2/1990 | Sebastian et al. | 128/878 |
| 4,966,137 | 10/1990 | Davini | 128/87 |
| 5,014,689 | 5/1991 | Meunchen et al. | 128/77 |
| 5,031,640 | 7/1991 | Spitzer | 128/878 |
| 5,160,314 | 11/1992 | Peters | 128/77 |
| 5,397,296 | 3/1995 | Syder et al. | 602/21 |
| 5,413,553 | 5/1995 | Downes | 602/21 |
| 5,437,620 | 8/1995 | Shelly | 602/21 |
| 5,466,215 | 11/1995 | Lair et al. | 602/21 |
| 5,538,501 | 7/1996 | Caswell | 602/64 |
| 5,643,186 | 7/1997 | Chinchalker | 601/40 |

OTHER PUBLICATIONS

Koch and Mason p.13 Purposeful Splinting Following injuries of hand, Jan. 1939 pp. 6–16.

David B. Siegel, MD et al., Anatomic Investigation of the Role of the Lumbrical Muscles in Carpal Tunnel Syndrome, Sep. 5, 1995, 860–63.

Tyson K. Cobb, MD, et al., Effect of Lumbrical Muscle Incursion Within the Carpal Tunnel on Carpal Tunnel Pressure: A Cadaveric Study, Mar. 2, 1995, 186–91.

*Primary Examiner*—Jerome Donnelly
*Attorney, Agent, or Firm*—Arnold B. Silverman; Benjamin T. Queen, II; Eckert Seamans Cherin & Mellott, LLC

[57] ABSTRACT

A uniquely configured splint designed to effect intrinsic muscle stretching includes a splint base and a splint tower. The splint base is secured to the arm of the person using the same. A palmar arch support is securable to the palm of the user and an end portion of the splint. The end portion of the splint has an upwardly projecting tower to which a finger supporting structure is secured. In use, the proximal and interphalangeal joints of the fingers are maintained in flexion and a force is exerted toward metacarpal phalangeal joint extension. This serves to stretch the intrinsic muscles of the hand. In order to accomplish this without also translating the flexor digitorum profundus tendon anteriorly, a palmar arch support is provided. The tower preferably generally overlies the palmar arch support. An associated method is disclosed.

10 Claims, 3 Drawing Sheets

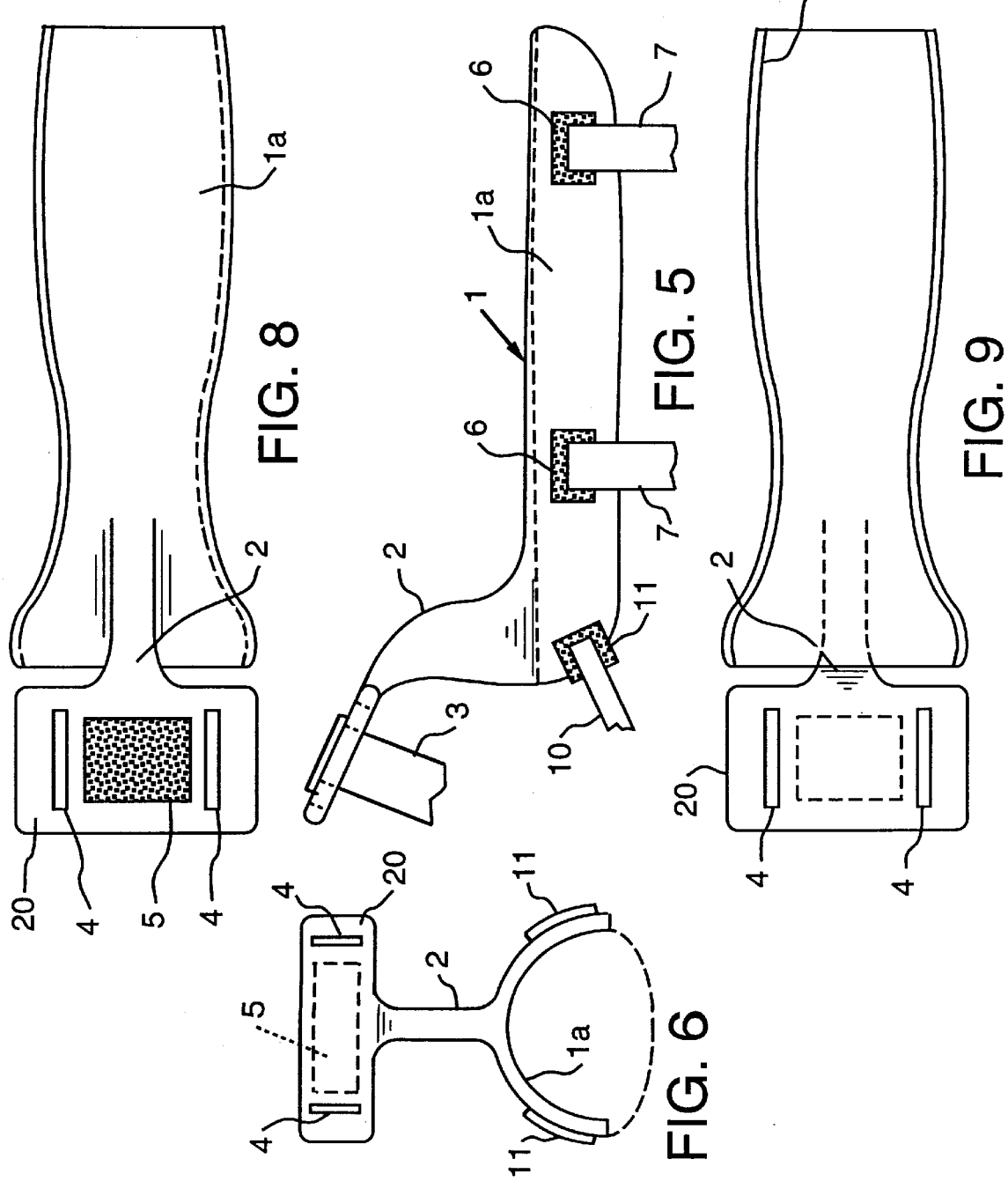

APPARATUS FOR EFFECTING STRETCHING OF INTRINSIC MUSCLES AND AN ASSOCIATED METHOD

BACKGROUND OF THE INVENTION

1. Field of the Invention

The present invention relates to apparatus and an associated method for applying a stretching force to the intrinsic muscles of a person in order to provide a prophylactic or therapeutic benefit.

2. Description of the Prior Art

According to the United States Bureau of Labor Statistics, carpal tunnel syndrome is the number one cause of occupational cumulative trauma injury in the United States. It is also the fastest growing cumulative trauma injury with over 200,000 new cases reported each year in the United States. According to the National Institute of Safety and Health, carpal tunnel syndrome costs are about at $3,000 per case in employee benefits and up to $40,000 per case in direct medical costs. The median job time lost is from a case of carpal tunnel syndrome is 20 days according to the Bureau of Labor Statistics.

Numerous strategies have been proposed to treat or prevent carpal tunnel syndrome. Prevention efforts have consisted of modification of work, home, or avocational activities (Ergonomics). Currently, the most widely accepted non-surgical treatments include wrist splinting, non-steroidal anti-inflammatory medication and local steroid injection. The use of ice, massage, acupuncture and electromodalities have also been employed. When conservative treatment is not effective, surgical division of the transverse carpal ligament is typically recommended. Although statistics are not available, the success rate of conservative treatment is not perceived to be great. Surgical treatment is not always effective and can lead to post-surgical problems, such as reflex sympathetic dystrophy.

Examples of known specific devices that have been designed to prevent or treat carpal tunnel syndrome are various gloves, padding, splints and bandages. Davini U.S. Pat. No. 4,966,137 discloses a splint system consisting of rigid and elastic components applied circumferentially around the wrist. In theory, the device exerts a force to move the radius and ulna closer to each other and, therefore, reduce tension in the transverse carpal ligament to reduce compression of the median nerve.

Downes U.S. Pat. No. 5,413,553 describes a carpal tunnel mitt that is worn like a glove and through a strapping arrangement attempts to approximate the medial and lateral ends of the transverse carpal ligament and thereby reduce tension in the ligament and decompress the median nerve. It is questionable whether either of these devices can overcome the connective tissue forces to accomplish decompression.

Nirsch U.S. Pat. No. 4,441,490, Sebastian et al. U.S. Pat. No. 4,899,763, Nelson U.S. Pat. No. 4,584,993 and Meanchen et al. U.S. Pat. No. 5,014,689 all disclose splints that by various means immobilize the wrist. Maintaining the wrist in a neutral position and restricting movement is thought to minimize pressure in the carpal canal. This type of immobilization has not met with a high success rate and has the further disadvantage of limiting the user's mobility for work or other activities.

U.S. Pat. No. 5,031,640 discloses a pad for preventing carpal tunnel syndrome. This device consists of a padded surface that is interposed between a tool and the user's hand. While this device may lessen point pressure over the median nerve during tool use, it does not represent a device that can provide long term relief of carpal tunnel syndrome.

There remains, therefore, a very real and substantial need for improved means for stretching of the intrinsic muscles so as to prevent or treat carpal tunnel syndrome, as well as for other purposes wherein such stretching action can have a valuable preventative or treating function.

SUMMARY OF THE INVENTION

The present invention has met the above-described needs by providing an apparatus which will stretch the intrinsic muscles which consist of the lumbrical muscles and the palmar and dorsal interossei muscles which are collectively referred to as the "intrinsic muscles." The proximal interphalangeal and distal interphalangeal joints of the fingers are maintained in a flexed position and the metacarpal phalangeal joints are positioned in an extended position. Anterior translation of the flexor digitorum profundus tendons is resisted during this process.

The apparatus includes a splint having a tower at one end with first securing means securing the splint to the arm of the person and a palmar arch support being secured at or adjacent one end of the splint by second securing means and finger receiving means being secured to the tower by third securing means.

In a preferred embodiment of the invention, the securing means are all adjustable, as by the use of Velcro, for example.

An associated method includes effecting the desired stretching of the intrinsic muscles while resisting undesired anterior translation of the flexor digitorum profundus tendons. This is accomplished by maintaining the proximal interphalangeal and distal interphalangeal joints in maximally flexed position and the metacarpal phalangeal joints in maximally extended position. The hereinbefore described splint is a preferred way to accomplish this objective.

It is, therefore, an object of the present invention to provide a device that provides controlled stretch to the lumbrical muscles and palmar and dorsal interossei muscles of the hand.

It is also an object of the current invention to provide a device effective in the prevention and treatment of carpal tunnel syndrome.

It is a further object of the invention to provide a device that can be applied to the user's arm during rest periods and as such does not interfere with functional activity.

It is yet another object of the invention to provide a device that can be utilized in hand therapy applications when stretching of the lumbrical muscles and palmar and dorsal interossei muscles of the hand is required.

Still further, it is an object of the invention to provide a device that can be applied simply and quickly by the individual user.

It is a further object of the present invention to provide an apparatus and associated method which will permit an individual who is not medically trained to provide stretching prophylactic or therapeutic treatments to themselves.

It is a further object of the present invention to provide such a system which will facilitate frequent use of the apparatus and method by unskilled or semi-skilled people without meaningful risk of their doing harm to themselves.

These and other objects of the invention will be more fully understood from the description of the invention on reference to the illustrations appended hereto.

BRIEF DESCRIPTION OF THE DRAWINGS

FIG. 5 is a front elevational view of the splint of FIG. 1.

FIG. 6 is a left-side elevation of the splint of FIG. 1.

FIG. 7 is a right-side elevational view of a form of the splint of FIG. 1.

FIG. 8 is a top plan view of the splint of FIG. 1.

FIG. 9 is a bottom plan view of the splint of FIG. 1.

DESCRIPTION OF THE PREFERRED EMBODIMENTS

Figure 1:
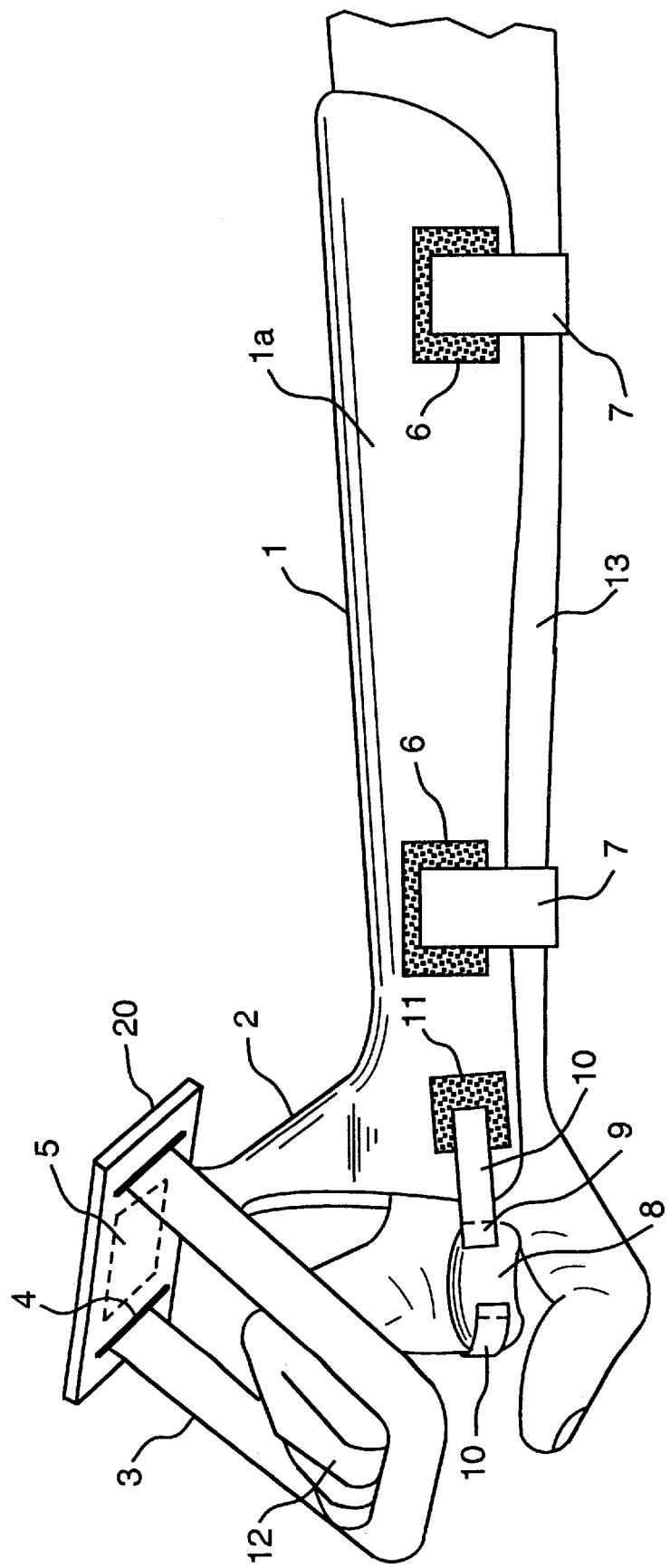
FIG. 1 is a partially schematic perspective view of a person's arm with a form of splint of the present invention secured thereto.

The intrinsic stretching splint of the present invention provides a means for stretching the palmar, dorsal interossei and lumbrical muscles of the hand.

The present invention is adapted for both prophylactic and therapeutic treatment of carpal tunnel syndrome to either resist the onset of the symptoms of the same or reduce the symptoms thereof.

The intrinsic stretching device provides a means of stretching the palmar and dorsal interossei and lumbrical muscles of the hand (commonly termed the "intrinsic muscles"). To stretch the intrinsic muscles, the proximal interphalangeal and the distal interphalangeal joints are maintained in a maximally flexed position and the metacarpal phalangeal joints are positioned in a maximally extended position. There is also the additional consideration of resisting the flexor digitorum profundus tendons translating anteriorly when stretching the intrinsics. To accomplish effective stretching of the intrinsic musculature, the present invention has a splint base with an integral support tower, a palmar arch support and associated Velcro and strapping. An elastic strap provides a means of maintaining the proximal interphalangeal and distal interphalangeal joints in flexion while extending the metacarpal phalangeal joints. A palmar arch support which is shaped to approximate the natural arch of the hand and which may be attached to the splint base with Velcro provides the restraint to resist excessive anterior translation of the flexor digitorum profundus tendon as the intrinsics are being stretched. The splint is designed to be worn for stretching purposes when the hand is not being used for functional activities. Over a period of time the splint or device will accomplish the goal of elongating the intrinsic muscles to prevent or reduce the symptoms of carpal tunnel syndrome. Stretching of the intrinsics can also be of value in other hand therapy applications.

Referring in greater detail to the figures, there is shown an elongated splint 1 which has a base 1a adjacent one end of which is an angularly upwardly projecting tower portion 2. The tower 2 terminates in a generally flat portion 20 having a pair of slots 4 and an interposed Velcro element 5 which is generally rectangular in shape and is secured to the upper surface of the splint 1. A strap 3 has Velcro elements secured to its free ends which pass through the slots 4 and are in engagement with Velcro element 5. Strap 3, which preferably is elastic, has portions which generally overlie palmar arch support 8. One or more of an individual's fingers 15 is secured within the splint opening defined between strap 3 and flat portion 20. The strap 3, which is preferably elastic, such that when tension is applied to the strap 3, a force is applied to the fingers that maintains the proximal interphalangeal and distal interphalangeal joints in a flexed position while an extension force is simultaneously applied by strap 3 to the metacarpal phalangeal joints of the fingers. This serves to effect a stretching force on the intrinsic muscles of the hand. In order to resist undesired translating of the flexor digitorum profundus tendon anteriorly a palmar arch support 8 is provided in the palm of the hand and is secured by strap means 10 (one not shown) to the splint 1 by Velcro elements 11 disposed on opposite sides of the splint 1 (one not shown) with the free ends 9 being secured to the palmar arch support 8 at Velcro locations 9. In this manner, the first strap 3 and the second straps 10 are adjustably secured to the splint 1. The palmar arch support 8 is preferably shaped to approximate the natural shape of the arch of the hand. This structure serves to apply as a dorsally directed force to the arch support and thereby to the palm of the hand. The splint body 1 is secured to the forearm 13 by straps 7 which contain Velcro elements on their ends which in turn are secured to Velcro elements 6 disposed on both sides of the splint 1 to thereby provide for intimate interrelationship between the splint 1 and the arm 16.

It will be appreciated that the Velcro securement of straps 3, 7, 10 provide securing means which are adjustable. In a preferred embodiment of the invention, strap 3 is at least in part composed of an elastic material while straps 7, 10 need not be elastic.

While Velcro is a preferred form of securing means to secure the straps to the splint 1, it will be appreciated that other means providing the adjustability, such as belts having the capability of being fastened at several locations may also be employed, for example.

Figure 2:
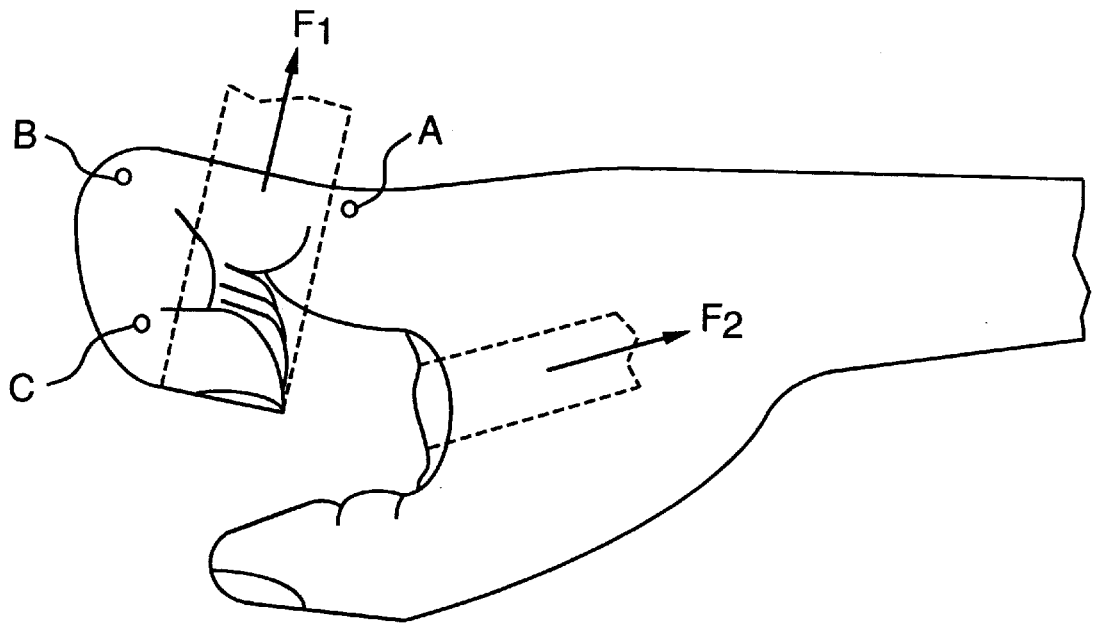
FIG. 2 is an elevational view of the hand in the position it assumes in the splint of FIG. 1.
Figure 3:
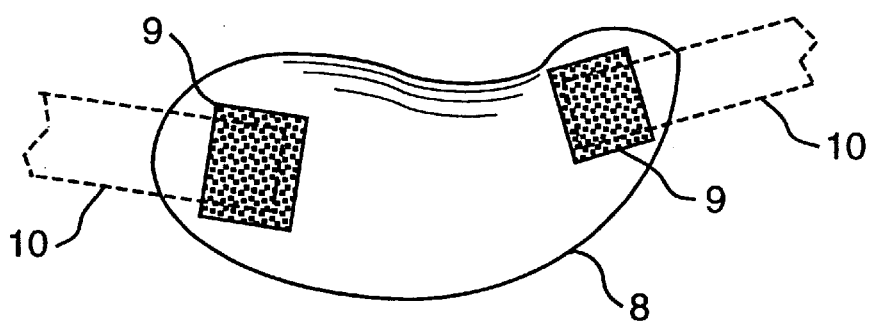
FIG. 3 is a schematic elevational view of a palmar arch support of the invention.
Figure 4:
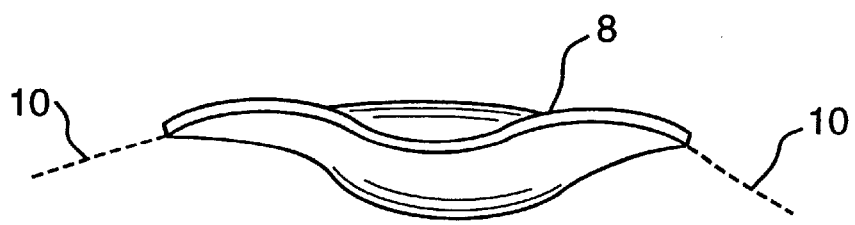
FIG. 4 is a bottom plan view of the palmar arch support of FIG. 2.

Referring to FIG. 2, the metacarpal phalangeal joint is identified by the letter A, the proximal interphalangeal joint is identified by the letter B, and the distal interphalangeal joint is identified by the letter C. Forces $F_1$ and $F_2$ are applied by strap 3 and palmar arch support 8, respectively.

The method of the present invention involves applying stretching forces to the intrinsic muscles, while simultaneously resisting undesired anterior translation of the flexor tendons and thereby reducing undesired compression of the median nerve. This is accomplished by providing forces to the hand which cause flexion of the proximal and distal interphalangeal joints and extension of the metacarpal phalangeal joints of the fingers while employing a palmar arch support to resist undesired excessive anterior translation of the flexor digitorum profundus tendon. The median nerve lies on top of the flexor digitorum profundus and flexor digitorum superficialis tendons and underneath the transverse carpal ligament. As a result, anterior translation of the flexor tendons will result in undesired compression of the median nerve. By contrast, controlled gradual lengthening of the lumbrical muscles will have the effect of reducing anterior translation of the flexor digitorum profundus tendons and thereby reduce compression of the median nerve.

In the method of this invention, a preferred practice is to employ a splint of the type hereinbefore disclosed.

It is preferred that the method of the invention be employed when the individual need not use the hand for other purposes. For example, the stretching may be applied for a period of about 0.5 to 1 hour at intervals at about 4 to 6 hours. It will be appreciated that dependent upon whether the condition is carpal tunnel syndrome or another condition and whether the use is prophylactic or therapeutic sound medical practice may dictate another approach to establishing times for this treatment.

It will be appreciated, therefore, that the present invention provides an effective means for stretching the intrinsic muscles in such a manner as to prophylactically or therapeutically provide beneficial treatment to a person. This may be accomplished in a simple manner not requiring skilled medical personnel to be involved on an ongoing regular basis.

Whereas particular embodiments of the invention have been described above for purpose of illustration, it will be appreciated by those skilled in the art that numerous variations of the details may be made without departing from the invention as described in the appended claims.

I claim:

1. Apparatus for stretching the intrinsic hand muscles comprising, a splint having a base and a tower, first securing means for securing said splint to a person's arm, a palmar arch support securable to said splint base, second securing means for securing said palmar arch support to said splint base, finger engaging means for stretching the intrinsic hand muscles, said finger engaging means secured to said splint tower, and third securing means for securing said finger engaging means to said splint tower.

2. The intrinsic hand muscle stretching apparatus of claim 1 including said finger engaging means being disposed in generally overlying relationship with respect to said palmar arch support.

3. The intrinsic hand muscle stretching apparatus of claim 1 including said finger engaging means structured to maintain the proximal and distal interphalangeal joints of the hand in flexion.

4. The intrinsic hand muscle stretching apparatus of claim 3 including said palmar arch support being structured to resist translation of the flexor digitorum profundus tendon anteriorly.

5. The intrinsic hand muscle stretching apparatus of claim 1 including said second securing means and said first securing means being adjustably secured to said splint base.

6. The intrinsic hand muscle stretching apparatus of claim 5 including said second securing means and third securing means including Velcro means.

7. The intrinsic hand muscle stretching apparatus of claim 1 including said finger engaging means being elastic.

8. The intrinsic hand muscle stretching apparatus of claim 1 including said finger engaging means structured to extend the metacarpal phalangeal joints.

9. The intrinsic hand muscle stretching apparatus of claim 1 including said splint being elongated, said tower being disposed adjacent a first end thereof, and said palmar arch support being disposed adjacent said first end.

10. The intrinsic hand muscle stretching apparatus of claim 9 including said tower being generally flat and having openings for passage of said third securing means therethrough.

* * * * *

UNITED STATES PATENT AND TRADEMARK OFFICE
CERTIFICATE OF CORRECTION

PATENT NO. : 5,976,058
DATED : November 2, 1999
INVENTOR(S) : Norman P. Gustafson It is certified that error appears in the above-identified patent and that said Letters Patent is hereby corrected as shown below:

Column 1,
Line 21, delete the word "is" after "lost".

Signed and Sealed this

Fourth Day of December, 2001

*Attest:*

NICHOLAS P. GODICI
*Attesting Officer*     Acting Director of the United States Patent and Trademark Office